United States Patent [19]

Jelich et al.

[11] Patent Number: 4,666,933
[45] Date of Patent: May 19, 1987

[54] (O-SUBSTITUTED OXIMINO)-PYRAZOLIN-5-ONE PESTICIDES

[75] Inventors: Klaus Jelich; Wolfgang Krämer, both of Wuppertal; Wilhelm Brandes, Leichlingen; Gerd Hänssler; Paul Reinecke, both of Leverkusen, all of Fed. Rep. of Germany

[73] Assignee: Bayer Aktiengesellschaft, Leverkusen, Fed. Rep. of Germany

[21] Appl. No.: 875,129

[22] Filed: Jun. 17, 1986

Related U.S. Application Data

[63] Continuation-in-part of Ser. No. 734,983, May 9, 1985, abandoned.

[30] Foreign Application Priority Data

May 23, 1984 [DE]  Fed. Rep. of Germany ....... 3419136
Dec. 21, 1984 [DE]  Fed. Rep. of Germany ....... 3446876

[51] Int. Cl.⁴ ................... A01N 43/56; C07D 231/46
[52] U.S. Cl. ...................................... 514/404; 548/365
[58] Field of Search ......................... 548/365; 514/404

[56] References Cited

U.S. PATENT DOCUMENTS 2,510,696  6/1950  Hunter et al. ...................... 514/404

OTHER PUBLICATIONS

Freri, Chem. Abst., 30, 6388³ (1936).
Dimroth et al., Chem. Abst., 3, 537² (1909).
Curtius: "Deriv. d. Diamides m. geschloss. Atomgruppir" Journal fur Prakt. Chemie. Bd. 50 (1894), p. 512ff.

Chemical Abstracts, vol. 86, No. 19, 5/9/77, pp. 552–554, Abstract No. 86:139927b.
Chemical Abstracts, vol. 97, No. 5, 8/2/82, p. 569, Abstract No. 38878h.

Primary Examiner—Richard A. Schwartz
Assistant Examiner—Kurt G. Briscoe
Attorney, Agent, or Firm—Sprung Horn Kramer & Woods

[57] ABSTRACT

Fungicidally active substituted pyrazolin-5-ones of the formula

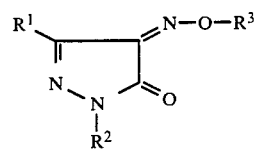

in which
R¹ is hydrogen or alkyl,
R² is hydrogen, alkyl, alkenyl, alkinyl, cyanoalkyl, hydroxyalkyl, alkoxyalkyl, hydroxycarbonylalkyl or alkoxycarbonylalkyl, aminocarbonylalkyl, alkylaminocarbonylalkyl or dialkylaminocarbonylalkyl, or in each case optionally substituted oxiranylmethyl, aralkyl or aryl, and
R³ is alkyl, alkenyl, alkinyl, cyanoalkyl, hydroxyalkyl, alkoxyalkyl, hydroxycarbonylalkyl, alkoxycarbonylalkyl, cycloalkyl or cycloalkylalkyl, or in each case optionally substituted aralkyl, aryloxyalkyl or arylthioalkyl, but wherein R³ is methyl or ethyl only if R¹ and/or R² is not hydrogen or methyl.

12 Claims, No Drawings

(O-SUBSTITUTED OXIMINO)-PYRAZOLIN-5-ONE PESTICIDES

This is a continuation-in-part of application Ser. No. 734,983, filed May 9, 1985, now abandoned.

The invention relates to new substituted pyrazolin-5-ones, several processes for their preparation and their use as agents for combating pests.

It is already known that organic nitrogen compounds, such as, for example, zinc ethylene-1,2-bis-(dithiocarbamate), have fungicidal properties (compare, for example, R. Wegler "Chemie der Pflanzenschutz-und Schädlingsbekämpfungsmittel [Chemistry of Plant Protection Agents and Agents for Combating Pests], Springer Verlag Berlin, Heidelberg, New York 1970, Volume 2, page 65 et seq.).

However, the action of these compounds is not always completely satisfactory in all fields of use, especially when low amounts and concentrations are applied.

New substituted pyrazolin-5-ones of the general formula (I)

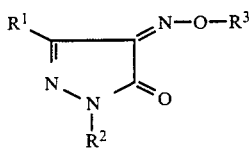

in which
R$^1$ represents hydrogen or alkyl,
R$^2$ represents hydrogen, alkyl, alkenyl, alkinyl, cyanoalkyl, hydroxylalkyl, alkoxyalkyl, hydroxycarbonylalkyl or alkoxycarbonylalkyl, aminocarbonylalkyl, alkylaminocarbonylalkyl, dialkylaminocarbonylalkyl, or in each case optionally substituted oxiranylmethyl, aralkyl or aryl and
R$^3$ represents alkyl, alkenyl, alkinyl, cyanoalkyl, hydroxyalkyl, alkoxyalkyl, hydroxycarbonylalkyl, alkoxycarbonylalkyl, cycloalkyl or cycloalkylalkyl, or in each case optionally substituted aralkyl, aryloxyalkyl or arylthioalkyl,
but wherein R$^3$ only represents methyl or ethyl if R$^1$ and/or R$^2$ do not simultaneously represent hydrogen or methyl, have been found.

The compounds of the formula (I) can be in the form of geometric isomers or isomer mixtures of different composition. Both the pure isomers and the isomer mixtures are claimed according to the invention.

It has furthermore been found that the new substituted pyrazolin-5-ones of the general formula (I)

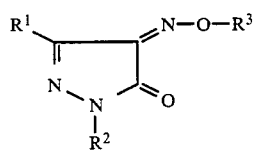

in which
R$^1$ represents hydrogen or alkyl,
R$^2$ represents hydrogen, alkyl, alkenyl, alkinyl, cyanoalkyl, hydroxyalkyl, alkoxyalkyl, hydroxycarbonylalkyl or alkoxycarbonylalkyl, aminocarbonylalkyl, alkylaminocarbonylalkyl, dialkylaminocarbonylalkyl, or in each case optionally substituted oxiranylalkyl, aralkyl or aryl and
R$^3$ represents alkyl, alkenyl, alkinyl, cyanoalkyl, hydroxyalkyl, alkoxyalkyl, hydroxycarbonylalkyl, alkoxycarbonylalkyl, cycloalkyl or cycloalkylalkyl, or in each case optionally substituted aralkyl, aryloxyalkyl or arylthioalkyl,
but wherein R$^3$ only represents methyl or ethyl if R$^1$ and/or R$^2$ do not simultaneously represent hydrogen or methyl, are obtained by a process in which (a) 4-oximino-pyrazolin-5-ones of the formula (II)

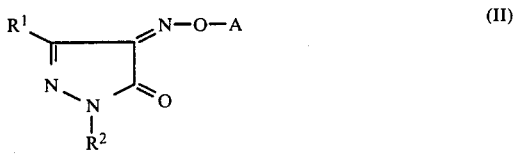

in which
R$^1$ and R$^2$ have the abovementioned meaning and
A represents hydrogen or an alkali metal cation,
are reacted with alkylating agents of the formula (III)

in which
R$^3$ has the abovementioned meaning and
X represents an electron-withdrawing leaving group,
if appropriate in the presence of a diluent, if appropriate in the presence of an acid-binding agent and if appropriate in the presence of a catalyst, or in which (b) the 4-alkoximino-pyrazolin-5-ones obtainable by process (a), of the formula (Ia)

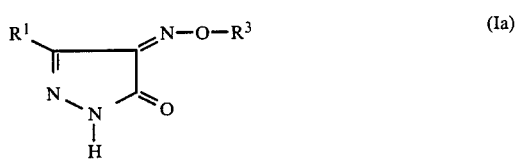

in which
R$^1$ and R$^3$ have the abovementioned meaning,
are reacted with alkylating agents of the formula (IV)

in which
R$^{2'}$ represents alkyl, alkenyl, alkinyl, cyanoalkyl, hydroxyalkyl, alkoxyalkyl, hydroxycarbonylalkyl or alkoxycarbonylalkyl or optionally substituted aralkyl or aryl and
Y represents an electron-withdrawing leaving group,
if appropriate in the presence of a diluent, if appropriate in the presence of an acid-binding agent and if appropriate in the presence of a catalyst.

Finally, it has been found that the new substituted pyrazolin-5-ones of the formula (I) have fungicidal and bactericidal properties.

Surprisingly, the new substituted pyrazolin-5-ones of the formula (I) exhibit better fungicidal properties than zinc ethylene-1,2-bis-dithiocarbamate, which is known from the prior art and is a closely related compound from the point of view of its action.

Formula (I) provides a general definition of the pyrazolin-5-ones according to the invention. Preferred compounds of the formula (I) are those in which $R^1$ represents hydrogen or straight-chain or branched alkyl with 1 to 8 carbon atoms, $R^2$ represents hydrogen, or represents in each case straight-chain or branched alkyl, alkenyl, alkinyl, cyanoalkyl, hydroxyalkyl, alkoxyalkyl, hydroxycarbonylalkyl, alkoxycarbonylalkyl, aminocarbonylalkyl, alkylaminocarbonylalkyl or dialkylaminocarbonylalkyl, with in each case up to 8 carbon atoms in the individual alkyl, alkenyl or alkinyl parts, or represents oxiranylalkyl with 1 to 4 carbon atoms in the straight-chain or branched alkyl part, or represents straight-chain or branched aralkyl which has 1 to 4 carbon atoms in the alkyl part and 6 to 10 carbon atoms in the aryl part and is optionally monosubstituted or polysubstituted by identical or different substituents, or represents aryl which has 6 to 10 carbon atoms and is optionally monosubstituted or polysubstituted by identical or different substituents, possible substituents in each case being: halogen, cyano, nitro, hydroxyl, in each case straight-chain or branched alkyl, alkoxy, dioxyalkylene, alkylcarbonyloxy and alkylthio with in each case up to 4 carbon atoms, straight-chain or branched halogenoalkyl, halogenalkoxy and halogenoalkylthio with in each case up to 4 carbon atoms and up to 9 identical or different halogen atoms, and phenyl, and $R^3$ represents straight-chain or branched alkyl with 1 to 20 carbon artoms, or represents in each case straight-chain or branched alkenyl, alkinyl, cyanoalkyl, hydroxyalkyl, alkoxyalkyl, hydroxycarbonylalkyl or alkoxycarbonylalkyl with in each case up to 8 carbon atoms in the individual alkyl, alkenyl or alkinyl parts, or represents cycloalkyl with 3 to 7 carbon atoms or cycloalkylalkyl with 3 to 6 carbon atoms in the cycloalkyl part and 1 or 2 carbon atoms in the alkyl part, or repesents arylalkyl, aryloxyalkyl or arylthioalkyl with in each case 1 to 4 carbon atoms in the individual alkyl parts and 6 to 10 carbon atoms in the aryl parts, and in each case optionally monosubstituted or polysubstituted by identical or different substituents, possible substituents being those mentioned for $R^2$, but wherein $R^3$ only represents methyl or ethyl if $R^1$ and $R^2$ do not simultaneously represent hydrogen or methyl.

Particularly preferred compounds of the formula (I) are those in which $R^1$ represents hydrogen, methyl, ethyl, n- or i-propyl or n-, i-, s- or t-butyl, $R^2$ represents hydrogen, methyl, ethyl, n- or i-propyl, n-, i-, s- or t-butyl, allyl, butenyl, propargyl, cyanomethyl, cyanoethyl, hydroxymethyl, hydroxyethyl, methoxymethyl, methoxyethyl, ethoxymethyl, ethoxyethyl, hydroxycarbonylmethyl, hydroxycarbonylethyl, methoxycarbonylmethyl, methoxycarbonylethyl, ethoxycarbonylmethyl or ethoxycarbonylethyl, aminocarbonylmethyl, methylaminocarbonylmethyl, ethylaminocarbonylmethyl, dimethylaminocarbonylmethyl, diethylaminocarbonylmethyl, aminocarbonylethyl, oxiranylmethyl, oxiranylethyl, or represents phenyl or benzyl, in each case optionally mono-, di- or tri-substituted by identical or different substituents, possible substituents being: fluorine, chlorine, bromine, iodine, cyano, nitro, hydroxyl, methyl, ethyl, n- or i-propyl, n-, i-, s- or t-butyl, methoxy, ethoxy, dioxymethylene, dioxyethylene, methylthio, ethylthio, acetoxy and propionyloxy, chloromethyl, dichloromethyl, trichloromethyl, trifluoromethyl, dichlorofluoromethyl, chlorodifluoromethyl, trifluoromethoxy, trifluoromethylthio and phenyl and $R^3$ represents methyl, ethyl, n- or i-propyl, n- or i-butyl, n- or i-pentyl, n- or i-hexyl, n- or i-heptyl, n- or i-octyl, n- or i-nonyl, n- or i-decyl, n- or i-dodecyl, n- or i-hexadecyl, allyl, butenyl, propargyl, cyanomethyl, cyanoethyl, hydroxymethyl, hydroxyethyl, methoxymethyl, methoxyethyl, ethoxymethyl, ethoxyethyl, hydroxycarbonylmethyl, hydroxycarbonylethyl, methoxycarbonylmethyl, methoxycarbonylethyl, ethoxycarbonylmethyl, ethoxycarbonylethyl, cyclopropyl, cyclopentyl, cyclohexyl or cyclohexylmethyl, or represents a radical of the formula $Ar-(Z)_m-(CH_2)_n-$,

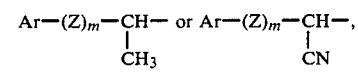

optionally mono-, di- or tri-substituted by identical or different substituents, wherein Ar in each case represents phenyl or naphthyl, Z in each case represents oxygen or sulphur, m in each case represents 0 or 1 and n represents 1, 2 or 3, possible substituents being those mentioned for $R^2$, with the restriction that $R^3$ only represents methyl or ethyl if $R^1$ and $R^2$ do not simultaneously represent hydrogen or methyl.

The following compounds of the general formula (I) may be mentioned specifically:

| $R^1$ | $R^2$ | $R^3$ |
|---|---|---|
| —CH₃ | —CH₃ | ⌬—⌬—CH₂— |
| —CH₃ | —CH₃ | 2,3,5,6-tetrachlorobenzyl—CH₂— |
| —C₂H₅ | —CH₃ | 2,4-dichlorophenyl—CH₂— |
| —C₂H₅ | —CH₃ | 4-NC-phenyl—CH₂— |
| —C₂H₅ | —CH₃ | 3-CN-phenyl—CH₂— |

-continued

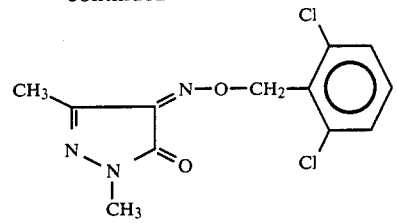

| $R^1$ | $R^2$ | $R^3$ |
|---|---|---|
| $-C_3H_7-n$ | $-CH_3$ | 2,3-Cl₂-C₆H₃-CH₂- |
| $-C_3H_7-n$ | $-CH_3$ | 4-NC-C₆H₄-CH₂- |
| $-C_3H_7-n$ | $-CH_3$ | 3-NC-C₆H₄-CH₂- |
| $-C_4H_9-n$ | $-CH_3$ | 2,3-Cl₂-C₆H₃-CH₂- |
| $-C_4H_9-n$ | $-CH_3$ | 4-NC-C₆H₄-CH₂- |
| $-C_4H_9-n$ | $-CH_3$ | 3-NC-C₆H₄-CH₂- |
| $-C_2H_5$ | $-CH_2-CN$ | 2,3-Cl₂-C₆H₃-CH₂- |
| $-C_3H_7-n$ | $-CH_2-CN$ | 2,3-Cl₂-C₆H₃-CH₂- |
| $-C_4H_9-n$ | $-CH_2-CN$ | 2,3-Cl₂-C₆H₃-CH₂- |
| $-CH_3$ | $-CH_3$ | C₆H₅-CH₂- |

If, for example, 4-hydroxyimino-1,3-dimethyl-pyrazolin-5-one and 2,6-dichlorobenzyl chloride are used as starting substances, the course of the reaction in process (a) according to the invention can be represented by the following equation:

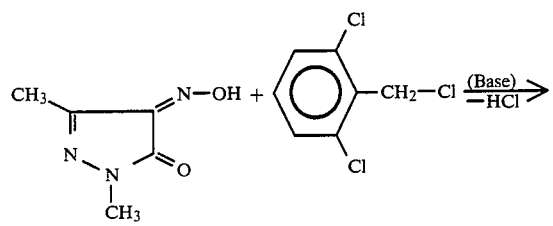

-continued

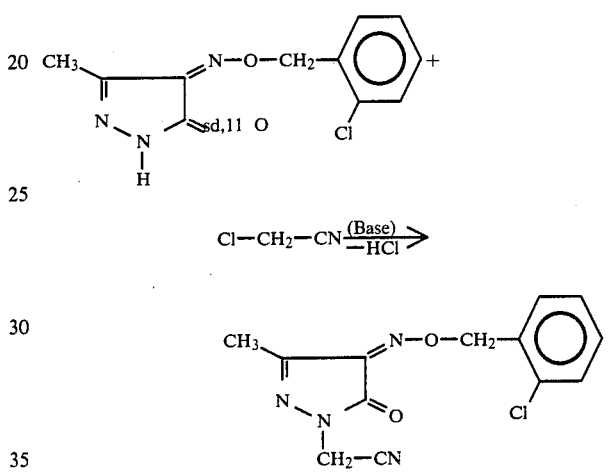

If, for example, 4-(2-chlorobenzyloximino)-3-methyl-pyrazolin-5-one and chloroacetonitrile are used as starting substances, the course of the reaction in process (b) according to the invention can be represented by the following equation:

Formula (II) provides a general definition of the 4-oximino-pyrazolin-5-ones required as starting substances for carrying out process (a) according to the invention. In this formula (II), $R^1$ and $R^2$ preferably represent those radicals which have already been mentioned as preferred for these substituents in the description of the substances of the formula (I) according to the invention. A preferably represents hydrogen or a sodium or potassium cation.

4-Oximino-pyrazolin-5-ones of the formula (II) are known [compare, for example, Ber. dtsch. chem. Ges. 29, 249 (1896) Coll. Czech. Chem. Commun. 25, 55 (1960); Arch. Pharm. 309, 900 ((1976) and Liebigs Ann. Chem. 1976, 1380]. They are obtained for example by a process in which β-keto esters of the formula (V)

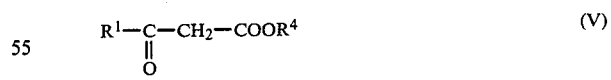

in which
$R^1$ has the abovementioned meaning and
$R^4$ represents lower alkyl, in particular methyl or ethyl,
are first cyclized, in a 1st stage, with hydrazines of the formula (VI)

in which
$R^2$ has the abovementioned meaning, if appropriate in the presence of a diluent, such as for example, ethanol to temperatures between 0° C. and 100° C., to product pyrazolin-5-ones of the formula (VII)

Alternatively, ethoxymethylenemalonic acid ester of the formula (Va)

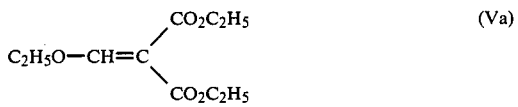

is first cyclized in a first stage with hydrazines of the formula (VI) and the resulting 4-ethoxycarbonyl-pyrazolin-5-ones of the formula (VIIa)

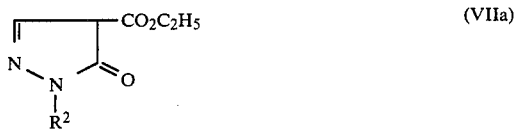

are saponified and decarboxylated, for example, with aqueous hydrochloric acid at temperatures between 50° C. and 120° C. to produce the pyrazolin-5-ones of the formula (VII) in which $R^1$ is hydrogen.

Then to produce (II), compounds (VII) are reacted in a final stage with a nitrosating agent, such as, for example, isopentyl nitrite or sodium nitrite, if appropriate in the presence of a diluent, such as, for example ethanol, water or aqueous hydrochloric acid, and if appropriate in the presence of a base, such as for example sodium ethylate, at temperatures between −20° C. and +50° C.

Formula (III) provides a general definition of the alkylating agents furthermore required as starting substances for carrying out process (a) according to the invention. In this formula (III), $R^3$ preferably represents those radicals which have already been mentioned as preferred for these substituents in the description of the substances of the formula (I) according to the invention. X preferably represents halogen, in particular chlorine, bromine or iodine, or optionally substituted alkylsulphonyloxy, alkoxysulphonyloxy or arylsulphonyloxy, such as, for example, methanesulphonyloxy, methoxysulphonyloxy, trifluoromethanesulphonyloxy or p-toluenesulphonyloxy.

The β-ketoester of the formula (V) and the ethoxymethylenmalonic acid ester of the formula (Va) are known compounds.

The alkylating agents of the formula (III) are generally known compounds of organic chemistry.

Formula (Ia) provides general definition of the 4-alkoximinopyrazolin-5-ones required as starting substances for carrying out process (b) according to the invention. In this formula (Ia), $R^1$ and $R^3$ preferably represent those radicals which have already been mentioned as preferred for these substituents in the description of the substances of the formula (I) according to the invention.

The 4-alkoximinopyrazolin-5-ones of the formula (Ia) are compounds according to the invention and can be obtained with the aid of process (a) according to the invention.

Formula (IV) provides a general definition of the alkylating agents furthermore required as starting substances for carrying out process (b) according to the invention. In this formula (IV), $R^{2'}$ preferably represents those radicals which have already been mentioned as preferred for the substituent $R^2$ in the description of the substances of the formula (I) according to the invention, with the exception of the hydrogen radical. Y preferably represents those leaving groups which have already been mentioned as preferred for the substituent X in the description of the alkylating agents of the formula (III).

The alkylating agents of the formula (IV) are also generally known compounds of organic chemistry.

Possible diluents for carrying out processes (a) and (b) according to the invention are inert organic solvents or aqueous systems.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform or carbon tetrachloride; ethers, such as diethyl ether, dioxane, tetrahydrofuran or ethylene glycol dimethyl or diethyl ether; ketones, such as acetone or butanone; nitriles, such as acetonitrile or propionitrile; amides, such as dimethylformamide, dimethylacetamide, N-methylformanilide, N-methylpyrrolidone or hexamethylphosphoric acid triamide; esters, such as ethyl acetate; sulphoxides, such as dimethylsulphoxide, or water or aqueous-organic two-phase mixtures, such as methylene chloride/water or toluene/water.

If appropriate, processes (a) and (b) according to the invention are carried out in the presence of an acid-binding agent.

Possible acid-binding agents are all the inorganic or organic bases which can usually be employed. These include, for example, alkali metal hydroxides, amides, alcoholates or hydrides, such as sodium hydroxide or potassium hydroxide, sodium ethylate or potassium t-butylate or sodium hydride or sodium amide, alkali metal carbonates, such as sodium carbonate or potassium carbonate, or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecane (DBU).

The reaction temperatures can be varied within a substantial range in carrying out processes (a) and (b) according to the invention. In general, the reaction is carried out at temperatures between −20° C. and +200° C., preferably at temperatures between 0° C. and +150° C.

In carrying out processes (a) and (b) according to the invention, in general 1.0 to 3.0 mols, preferably 1.0 to 1.5 mols, of alkylating agent of the formula (III) or (IV) and, if appropriate, 1.0 to 3.0 mols, preferably 1.0 to 1.5 mols, of acid-binding agents are in general employed per mol of 4-oximino-pyrazolin-5-one or in the formula (II) or (Ia).

If an organic-aqueous two-phase system is used, the reaction can be carried out, if appropriate, the presence of 0.1 to 1 mol of a suitable phase transfer catalyst, such as, for example, a quaternary ammonium or phosphonium compound. Examples which may be mentioned are triethylbenzylammonium chloride and benzyldodecyldimethylammonium chloride.

The reaction products of the formula (I) are worked up and isolated by customary methods.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are used in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Botrytis species, such as, for example, *Botrytis cinerea;* Plasmopara species, such as, for example, *Plasmopara viticola;* Uromyces species, such as, for example, *Uromyces appendiculatus;* Sphaerotheca species, such as, for example, *Sphaerotheca fuliginea;* Venturia species, such as, for example, *Venturia inaequalis;* Podosphaera species, such as, for example, *Podosphaera leucotricha;* Phytophthora species, such as, for example, *Phytophthora infestans;* Erysiphe species, such as, for example, *Erysiphe graminis;* Puccinia species, such as, for examlple *Puccinia recondita;* Fusarium species, such as, for example, *Fusarium culmorum;* Ustilago species, such as, for example, *Ustilago nuda* or *Ustilago avenae;* Septoria species, such as, for example, Septoria nodorum; Tilletia species, such as, for example, *Tilletia caries;* Xanthomonas species, such as, for example, *Xanthomonas oryzae;* Pseudomonas species, such as, for example, *Pseudomonas lachrymans;* Pyricularia species, such as, for example, *Pyricularia oryzae;* Pellicularia species, such as, for example, *Pellicularia sasakii* and Pyrenophora species, such as, for example, *Pyrenophora teres* (conidia form: Drechslera, syn: Helminthosphorium); Leptosphaeria species, such as, for example, *Leptosphaeria nodorum;* Cochliobolus species, such as, for example, *Cochliobolus sativus* (conidia form: Drechslera, syn: Helminthosporium) and Cercospora species, such as, for example, *Cercospora canescens.*

The good toleration, by plants, of the active compounds, at the concentrations required for combating plant diseases, permits treatment of above-ground parts of plants, of vegetative propagation stock and seeds; and of the soil.

The active compounds according to the invention can be used here with particularly good success for combating cereal diseases, such as, for example, those caused by *Cochliobolus sativus, Heptosphaeria nodorum,* species of Fusarium or *Pyrenophora teres,* rust causative organisms, against mildew causative organisms, for combating vegetable diseases, such as, for example, against the brown rot of tomato causative organism (*Phytophthora infestans*) or against the grey mould of beans causative organism (*Botrytis cinerea*), or for combating rice diseases, such as, for example against the rice spot disease causative organism (*Pyricularia oryzae*).

Besides an outstanding protective activity, the active compounds according to the invention also exhibit very good systemic properties. They are distinguished by a broad fungicidal in vitro action and by additional bactericidal properties.

The active compounds can be converted to the customary formulations, such as solutions, emulsions, suspensions, powders, dusts, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules and latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom by further dilution, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

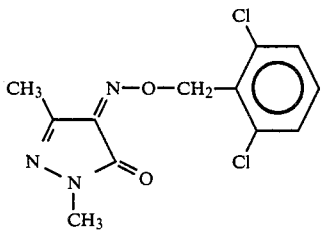

(Process a)

13.9 g (0.071 mol) of 2,6-dichlorobenzyl chloride in 30 ml of absolute dimethylformamide are added dropwise to 10 g (0.071 mol) of 1,3-dimethyl-4-hydroximino-pyrazolin-5-one and 7.2 g (0.071 mol) of triethylamine in 50 ml of absolute dimethylformamide at room temperature, with stirring, and, when the addition has ended, the mixture is stirred at room temperature for a further 24 hours.

For working up, the mixture is poured into 300 ml of water and extracted four times with 70 ml of chloroform each time. The combined organic phases are washed five times with 200 ml of water each time, dried over magnesium sulphate and concentrated in vacuo. The crystalline residue is triturated with a little ether and filtered off with suction. 9 g (42% of theory) of 1,3-dimethyl-4-(2,6-dichlorobenzyloximino)-pyrazolin-5-one of melting point 132° C. are obtained.

Preparation of the starting compound

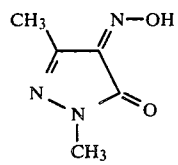

183 g (1.56 mol) of isopentyl nitrite are added dropwise to 175 g (1.56 mol) of 1,3-dimethyl-pyrazolin-5-one and 84.4 g (1.56 mol) of sodium methylate in 1 L of absolute ethanol, while stirring and cooling with ice so that the internal temperature does not rise above 25° C. to 30° C. When the addition has ended, stirring is continued at room temperature for 24 hours and the sodium salt of 1,3-dimethyl-4-hydroximino-pyrazolin-5-one which has precipitated is filtered off with suction. The crystalline product is dissolved in 1 L of water and the solution is acidified with glacial acetic acid. For complete precipitation, the mixture is cooled at 0° C. for several hours, and the product is then filtered off with suction. 162 g (74% of theory) of 1,3-dimethyl-4-hydroximino-pyrazolin-5-one of melting point 93° C. are obtained.

Example 2

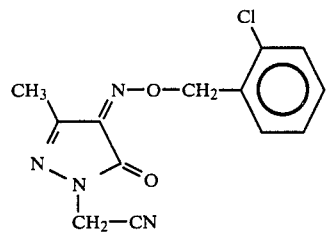

10 g (0.04 mol) of 4-(2-chlorobenzyloximino)-3-methylpyrazolin-5-one in 50 ml of absolute dimethylformamide are added dropwise to 1.6 g (0.053 mol) of sodium hydride (80 percent strength suspension in mineral oil) in 30 ml of absolute dimethylformamide at 0° C., while stirring and simultaneously passing over a dry stream of nitrogen, and, when the addition has ended, stirring is continued at 0° C. for one hour. Thereafter, 3.6 g (0.048 mol) of chloroacetonitrile are added dropwise, also at room temperature, and stirring is continued at 0° C. for 3 hours and then overnight at room temperature.

For working up, the excess sodium hydride is destroyed by careful addition of water and the mixture is then extracted four times with 80 ml of chloroform each time. The combined organic phases are washed five times with 200 ml of water each time, dried over magnesium sulphate and concentrated in vacuo.

The oil which remains is purified by column chromatography (silica gel/methylene chloride:ether 1:1), and the oil thus obtainable is crystallized by trituration with ether and the crystals are filtered off with suction. 3.7 g (32% of theory) of 4-(2-chlorobenzyloximino)-1-cyanomethyl-3-methyl-pyrazolin-5-one of melting point 118°-125° C. are obtained.

The following compounds of the general formula (I) are obtained in a corresponding manner according to the general preparation description:

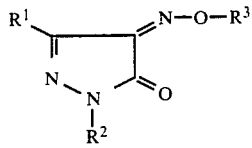
(I)

| Example No. | $R^1$ | $R^2$ | $R^3$ | Physical data [M.p. = melting point in °C.] |
|---|---|---|---|---|
| 3 | CH₃ | —CH₂—C≡CH | CH₃ | ¹H—NMR* 4.3 ppm |
| 4 | (CH₃)₃C— | H | CH₃ | ¹H—NMR* 4.3 ppm |
| 5 | CH₃ | H | —CH₂—CH=CH₂ | M.p. 56 |
| 6 | CH₃ | —CH₂—C₆H₄—Cl (o) | CH₃ | M.p. 96 |
| 7 | CH₃ | H | —CH₂—C₆H₄—Cl (o) | M.p. 130 |
| 8 | CH₃ | CH₃ | —CH₂—CH=CH₂ | ¹H—NMR* 4.9 ppm |
| 9 | CH₃ | CH₃ | —CH₂—C₆H₄—Cl (o) | M.p. 104 |
| 10 | CH₃ | —CH₂—CH=CH₂ | CH₃ | ¹H—NMR* 4.3 ppm |
| 11 | CH₃ | —CH₂—CN | CH₃ | ¹H—NMR* 4.3 ppm |
| 12 | CH₃ | H | —CH₂—C₆H₅ | ¹H—NMR* 5.5 ppm |
| 13 | CH₃ | H | —CH(CN)—C₆H₅ | ¹H—NMR* 2.1 ppm |
| 14 | CH₃ | CH₃ | —CH(CN)—C₆H₅ | M.p. 167 |
| 15 | CH₃ | —CH₂—OC₂H₅ | —CH₂—C₆H₄—Cl (o) | ¹H—NMR* 5.0 and 5.6 ppm |
| 16 | CH₃ | CH₃ | —CH₂—C₆H₃—Cl₂ (3,4) | M.p. 98 |
| 17 | CH₃ | CH₃ | —CH₂—C₆H₅ | ¹H—NMR* 5.5 ppm |
| 18 | CH₃ | CH₃ | —CH₂—C₆H₄—Cl (p) | M.p. 98 |
| 19 | CH₃ | CH₃ | —CH₂—C₆H₄—CH₃ (p) | ¹H—NMR* 5.4 ppm |
| 20 | CH₃ | CH₃ | —CH₂—C₆H₄—NO₂ (p) | M.p. 130 |
| 21 | CH₃ | CH₃ | —CH₂—CH₂—C₆H₅ | ¹H—NMR* 4.7 ppm |
| 22 | CH₃ | CH₃ | —CH₂—C≡CH | M.p. 110-112 |

-continued

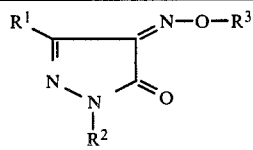
(I)

| Example No. | R¹ | R² | R³ | Physical data [M.p. = melting point in °C.] |
|---|---|---|---|---|
| 23 | $CH_3$ | $-CH(CH_3)_2$ | $-CH_2-C_6H_4-Cl$ (o) | M.p. 95 |
| 24 | $CH_3$ | $-CH_2-COOC_2H_5$ | $-CH_2-C_6H_4-Cl$ (o) | $^1H-NMR^*$ 4.5 and 5.6 ppm |
| 25 | $CH_3$ | $-CH_2-CH_2-OH$ | $-CH_2-C_6H_4-Cl$ (o) | M.p. 89 |
| 26 | $CH_3$ | H | $-CH_2-C_6H_3-Cl_2$ (3,4) | M.p. 147 |
| 27 | $CH_3$ | $-CH_2-COOH$ | $-CH_2-C_6H_4-Cl$ (o) | M.p. 118–125 |
| 28 | $CH_3$ | $CH_3$ | $-(CH_2)_4-CH_3$ | $^1H-NMR^*$ 4.5 ppm |
| 29 | $CH_3$ | $CH_3$ | $-(CH_2)_2-CH_3$ | $^1H-NMR^*$ 4.4 ppm |
| 30 | $CH_3$ | $CH_3$ | $-CH(CH_3)_2$ | M.p. 86 |
| 31 | $CH_3$ | $CH_3$ | $-CH_2-CH_2-CH(CH_3)_2$ | $^1H-NMR^*$ 4.5 ppm |
| 32 | $CH_3$ | $CH_3$ | $-CH_2-COOC_2H_5$ | M.p. 66–68 |
| 33 | $CH_3$ | $CH_3$ | $-C_6H_{11}$ | $^1H-NMR^+$ 4.5 ppm |
| 34 | $CH_3$ | H | $-CH_2-C_6H_4-Cl$ (p) | M.p. 146–151 |
| 35 | $CH_3$ | $CH_3$ | $-(CH_2)_3-CH_3$ | $^1H-NMR^*$ 4.5 ppm |
| 36 | $CH_3$ | $CH_3$ | $-(CH_2)_{11}-CH_3$ | $^1H-NMR^*$ 4.5 ppm |
| 37 | $CH_3$ | H | $-CH(CH_3)_2$ | M.p. 92 |
| 38 | H | $CH_3$ | $-CH_2-C_6H_4-Cl$ (o) | M.p. 77–80 |
| 39 | $CH_3$ | H | $-C_6H_{11}$ | M.p. 100 |
| 40 | $CH_3$ | $CH_3$ | $-CH_2-C_6H_3(NO_2)(OH)$ | M.p. 137 |
| 41 | $CH_3$ | H | $-(CH_2)_3-CH_3$ | M.p. 65–68 |
| 42 | $CH_3$ | H | $-(CH_2)_{11}-CH_3$ | M.p. 77 |
| 43 | $CH_3$ | $CH_3$ | $-CH_2-C_6H_4-Cl$ (m) | M.p. 90 |

-continued

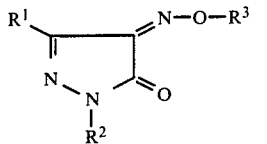
(I)

| Example No. | R¹ | R² | R³ | Physical data [M.p. = melting point in °C.] |
|---|---|---|---|---|
| 44 | $CH_3$ | $CH_3$ | —$CH_2$—C₆H₄—$OCH_3$ | ¹H—NMR* 5.4 ppm |
| 45 | $CH_3$ | $CH_3$ | —$CH_2$—C₆H₄—O—C(=O)—$CH_3$ | M.p. 101–104 |
| 46 | $CH_3$ | $CH_3$ | —$CH_2$—C₆H₃(Cl)(F) | M.p. 144 |
| 47 | $CH_3$ | $CH_3$ | —$CH_2$—C₆H₃($CH_3$)($CH_3$) | M.p. 84–88 |
| 48 | $CH_3$ | $CH_3$ | —$CH_2$—C₆H₃($CH_3$)($CH_3$) | ¹H—NMR* 5.4 ppm |
| 49 | $CH_3$ | $CH_3$ | —$CH_2$—C₆H₄—$CH_3$ | M.p. 102 |
| 50 | $CH_3$ | $CH_3$ | —$CH_2$—C₆H₄—$CH_2$Cl | ¹H—NMR* 5.6 ppm |
| 51 | $CH_3$ | $CH_3$ | —$CH_2$-naphthyl | M.p. 119 |
| 52 | $CH_3$ | $C_2H_5$ | —$CH_2$—C₆H₄—Cl | ¹H—NMR* 5.6 ppm |
| 53 | $CH_3$ | $CH_3$ | —$CH_2$—C₆H₃($CH_3$)($CH_3$) | ¹H—NMR* 5.4 ppm |
| 54 | $CH_3$ | $CH_3$ | —$(CH_2)_5$—$CH_3$ | ¹H—NMR* 4.5 ppm |
| 55 | $CH_3$ | $CH_3$ | —$(CH_2)_7$—$CH_3$ | ¹H—NMR* 4.5 ppm |
| 56 | $CH_3$ | $CH_3$ | —$(CH_2)_9$—$CH_3$ | ¹H—NMR* 4.5 ppm |
| 57 | $CH_3$ | $CH_3$ | —$(CH_2)_{15}$—$CH_3$ | M.p. 28 |
| 58 | $CH_3$ | $CH_3$ | —$CH_2$—C₆H₄—CN | M.p. 126 |

-continued

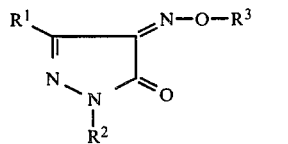

| Example No. | R¹ | R² | R³ | Physical data [M.p. = melting point in °C.] |
|---|---|---|---|---|
| 59 | CH₃ | CH₃ | —CH₂—C₆H₄—CN (meta) | M.p. 126 |
| 60 | CH₃ | CH₃ | —CH₂—C₆H₄—CN (para) | M.p. 158 |
| 61 | CH₃ | CH₃ | —CH(CH₃)—C₆H₅ | ¹H—NMR* 5.7 ppm |
| 62 | CH₃ | —C₆H₅ | —CH₂—C₆H₄—Cl | M.p. 120 |
| 63 | CH₃ | —C₆H₅ | —CH₂—CN | M.p. 135 |
| 64 | CH₃ | CH₃ | —CH₂—C₆H₄—CF₃ | M.p. 60 |
| 65 | CH₃ | —C₆H₅ | CH₃ | M.p. 98 |
| 66 | CH₃ | —C₆H₅ | —CH₂—COOH | M.p. 139 |
| 67 | CH₃ | —C₆H₅ | —C₆H₁₁ (cyclohexyl) | ¹H—NMR* 4.5 ppm |
| 68 | CH₃ | H | —CH₂—C₆H₃(CH₃)₂ (2,3-dimethyl) | ¹H—NMR* 5.5 ppm |
| 69 | CH₃ | H | —CH₂—C₆H₄—CF₃ | ¹H—NMR* 5.5 ppm |
| 70 | CH₃ | H | —CH₂—C₆H₄—Cl | ¹H—NMR* 5.4 ppm |
| 71 | CH₃ | H | —CH₂—C₆H₃(F)(Cl) | M.p. 133 |
| 72 | CH₃ | H | —CH₂—C₆H₄—Br | ¹H—NMR* 5.5 ppm |
| 73 | CH₃ | H | —CH₂—C₆H₃(CH₃)₂ | ¹H—NMR* 5.5 ppm |

-continued

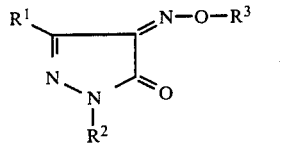
(I)

| Example No. | R¹ | R² | R³ | Physical data [M.p. = melting point in °C.] |
|---|---|---|---|---|
| 74 | $CH_3$ | $-CH_2-CN$ | $-CH_2-$⟨4-Cl-C₆H₄⟩ | $^1$H—NMR* 4.6 and 5.5 ppm |
| 75 | $CH_3$ | H | $-CH_2-$⟨2,3-Cl₂-C₆H₃⟩ | M.p. 115–120 |
| 76 | $CH_3$ | $-CH_2-CN$ | $-CH_2-$⟨3,4-Cl₂-C₆H₃⟩ | $^1$H—NMR* 4.6 and 5.4 ppm |
| 77 | $CH_3$ | $-CH_2-CN$ | $-CH_2-$⟨3-Cl-C₆H₄⟩ | $^1$H—NMR* 4.6 and 5.5 ppm |
| 78 | $CH_3$ | $-CH_2-CH_2-CN$ | $-CH_2-$⟨2-Cl-C₆H₄⟩ | M.p. 58 |
| 79 | $CH_3$ | $-CH_2-CH_2-CN$ | $-CH_2-$⟨4-Cl-C₆H₄⟩ | M.p. 101 |
| 80 | $CH_3$ | $-CH_2-CN$ | $-CH_2-$⟨3,4-(CH₃)₂-C₆H₃⟩ | $^1$H—NMR* 4.6 and 5.5 ppm |
| 81 | $CH_3$ | $-CH_2-CN$ | $-CH_2-$⟨3,5-(CH₃)₂-C₆H₃⟩ | $^1$H—NMR* 4.6 and 5.5 ppm |
| 82 | $CH_3$ | $-CH_2-CH_2-CN$ | $-CH_2-$⟨3,4-Cl₂-C₆H₃⟩ | M.p. 120 |
| 83 | $CH_3$ | $-CH_2-CH_2-CN$ | $-CH_2-$⟨3,5-Cl₂-C₆H₃⟩ | M.p. 106 |
| 84 | $CH_3$ | $-CH_2-CN$ | $-CH_2-$⟨3-CF₃-C₆H₄⟩ | $^1$H—NMR* 4.6 and 5.5 ppm |
| 85 | $CH_3$ | $-CH_2-CN$ | $-CH_2-$⟨4-Br-C₆H₄⟩ | $^1$H—NMR* 4.6 and 5.5 ppm |
| 86 | $CH_3$ | $-CH_2-CN$ | $-CH_2-$⟨2-F,5-Cl-C₆H₃⟩ | $^1$H—NMR* 4.6 and 5.7 ppm |

-continued

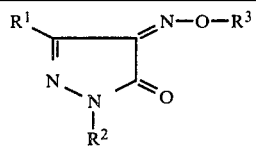

| Example No. | R¹ | R² | R³ | Physical data [M.p. = melting point in °C.] |
|---|---|---|---|---|
| 87 | CH₃ | —CH₂—CN | —CH₂—C₆H₃(Cl)(Cl) (2,3-dichlorobenzyl) | ¹H—NMR* 4.6 and 5.5 ppm |
| 88 | CH₃ | CH₃ | —CH₂—C₆H₄—CF₃ (4-) | ¹H—NMR* 5.5 ppm |
| 89 | CH₃ | CH₃ | —CH₂—C₆H₄—CF₃ (3-) | M.p. 72 |
| 90 | CH₃ | CH₃ | —CH₂—C₆H₃(Cl)(CF₃) | M.p. 87 |
| 91 | CH₃ | CH₃ | —CH₂—C₆H₃(OCF₃)(Cl) | M.p. 63–67 |
| 92 | CH₃ | CH₃ | —CH₂—C₆H₄—Br (4-) | M.p. 103 |
| 93 | CH₃ | CH₃ | —CH₂—C₆H₄—Br (2-) | M.p. 90 |
| 94 | CH₃ | CH₃ | —CH₂—C₆H₄—I (3-) | M.p. 103–106 |
| 95 | CH₃ | CH₃ | —CH₂—C₆H₃(Cl)(Cl) (2,3-dichlorobenzyl) | M.p. 111 |
| 96 | CH₃ | CH₃ | —CH₂—C₆H₄—Br (3-) | M.p. 101 |
| 97 | CH₃ | CH₃ | —CH₂—C₆H₃(Cl)(F) | M.p. 95 |
| 98 | CH₃ | CH₃ | —CH₂—C₆H₃(Cl)(CF₃) | M.p. 68–72 |
| 99 | CH₃ | CH₃ | —CH₂—C₆H₄—SCF₃ | ¹H—NMR* 5.55 ppm |
| 100 | CH₃ | —CH₂—CH₂—CN | —CH₂—C₆H₄—CF₃ | M.p. 79 |

-continued

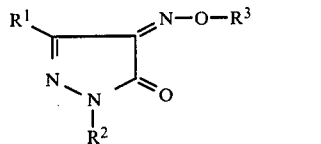

(I)

| Example No. | $R^1$ | $R^2$ | $R^3$ | Physical data [M.p. = melting point in °C.] |
|---|---|---|---|---|
| 101 | $CH_3$ | $-CH_2-CH_2-CN$ | $-CH_2-$(3-Cl, 4-$CF_3$-phenyl) | M.p. 70–75 |
| 102 | $CH_3$ | $CH_3$ | $-CH_2-$(3-F-phenyl) | M.p. 64 |
| 103 | $CH_3$ | $CH_3$ | $-CH_2-$(2-F-phenyl) | M.p. 75–80 |
| 104 | $CH_3$ | $CH_3$ | $-CH_2-$(4-F-phenyl) | $^1$H—NMR* 5.45 ppm |
| 105 | $CH_3$ | H | $-CH_2-$(3-Cl, 4-$CF_3$-phenyl) | M.p. 123 |
| 106 | $CH_3$ | $CH_3$ | $-CH_2-O-$(4-Cl-phenyl) | M.p. 88 |
| 107 | $CH_3$ | $-CH_2-CH_2-CN$ | $-CH_2-$(4-Br-phenyl) | M.p. 90 |
| 108 | $CH_3$ | $CH_3$ | $-CH_2-$(4-Cl-3,4-methylenedioxyphenyl) | M.p. 125 |
| 109 | $C_2H_5$ | $CH_3$ | $-CH_2-$(3,4-Cl$_2$-phenyl) | $^1$H—NMR* 5.5 ppm |
| 110 | $CH_3$ | $CH_3$ | $-CH_2-$(4-phenyl-phenyl) | $^1$H—NMR* 5.45 ppm |
| 111 | $CH_3$ | $CH_3$ | $-CH_2-$(2,3,4-Cl$_3$-phenyl) | M.p. 130 |
| 112 | $CH_3-(CH_2)_2-$ | $CH_3$ | (3,4-Cl$_2$-phenyl)$-CH_2-$ | M.p. 56 |
| 113 | $CH_3-(CH_2)_3-$ | H | (3,4-Cl$_2$-phenyl)$-CH_2-$ | M.p. 112 |

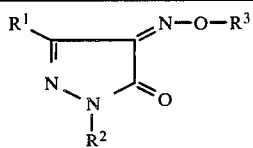

(I)

-continued

| Example No. | $R^1$ | $R^2$ | $R^3$ | Physical data [M.p. = melting point in °C.] |
|---|---|---|---|---|
| 114 | $C_2H_5$ | $CH_3$ | 2-Cl-C$_6$H$_4$-CH$_2$- | M.p. 58 |
| 115 | $CH_3-(CH_2)_2-$ | $CH_3$ | 2-Cl-C$_6$H$_4$-CH$_2$- | M.p. 58 |
| 116 | $CH_3-(CH_2)_2-$ | H | 3,4-Cl$_2$-C$_6$H$_3$-CH$_2$- | M.p. 104 |
| 117 | $C_2H_5-$ | $CH_3$ | 4-Cl-C$_6$H$_4$-CH$_2$- | M.p. 94 |
| 118 | $CH_3-(CH_2)_3-$ | $CH_3$ | 4-Cl-C$_6$H$_4$-CH$_2$- | M.p. 114 |
| 119 | $CH_3-(CH_2)_3-$ | $CH_3$ | 2-Cl-C$_6$H$_4$-CH$_2$- | M.p. 42 |
| 120 | $C_2H_5$ | H | 2-Cl-C$_6$H$_4$-CH$_2$- | M.p. 103 |
| 121 | $CH_3-(CH_2)_2-$ | H | 2-Cl-C$_6$H$_4$-CH$_2$- | M.p. 78 |
| 122 | $CH_3-(CH_2)_3-$ | H | 2-Cl-C$_6$H$_4$-CH$_2$- | M.p. 93 |
| 123 | $CH_3$ | $CH_3$ | cyclohexyl-CH$_2$- | Oil $^1$H—NMR* 4.3 ppm |
| 124 | $CH_3-(CH_2)_3-$ | $NC-CH_2-$ | 3,4-Cl$_2$-C$_6$H$_3$-CH$_2$- | Oil $^1$H—NMR* 5.35; 4.6 ppm |
| 125 | $CH_3-(CH_2)_3-$ | $NC-CH_2-$ | 2-Cl-C$_6$H$_4$-CH$_2$- | M.p. 55 |
| 126 | $C_2H_5$ | $NC-CH_2-$ | 2-Cl-C$_6$H$_4$-CH$_2$- | Oil $^1$H—NMR* 5.6; 4.6 ppm |

-continued

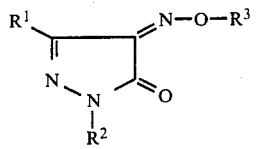

| Example No. | R¹ | R² | R³ | Physical data [M.p. = melting point in °C.] |
|---|---|---|---|---|
| 127 | $CH_3-(CH_2)_2-$ | $NC-CH_2-$ | 2-Cl-C₆H₄-CH₂- | Oil ¹H—NMR* 5.6; 4.5 ppm |
| 128 | $CH_3$ | 2-Cl-C₆H₄- | $NC-CH_2-$ | Oil ¹H—NMR* 5.0 ppm |
| 129 | $(CH_3)_3C-$ | $CH_3$ | $NC-CH_2-$ | Oil ¹H—NMR* 5.0 ppm |
| 130 | $CH_3-(CH_2)_3-$ | $CH_3$ | 4-Cl-C₆H₄-CH₂- | M.p. 40 |
| 131 | $CH_3$ | 4-CH₃-C₆H₄- | $NC-CH_2-$ | M.p. 91 |
| 132 | $CH_3$ | $(CH_3)_3C-$ | $NC-CH_2-$ | Oil ¹H—NMR* 5.0 ppm |
| 133 | $CH_3$ | H | 2,6-Cl₂-C₆H₃-CH₂- | M.p. 144 |
| 134 | $CH_3$ | H | 3-CH₃O-C₆H₄-CH₂- | M.p. 86 |
| 135 | $CH_3$ | H | 4-CH₃COO-C₆H₄-CH₂- | M.p. 109 |
| 136 | $CH_3$ | H | 2-CN-C₆H₄-CH₂- | M.p. 147 |
| 137 | $CH_3$ | H | 3-NC-C₆H₄-CH₂- | M.p. 140 |
| 138 | $CH_3$ | H | 4-NC-C₆H₄-CH₂- | M.p. 169 |
| 139 | $CH_3$ | $NC-CH_2-$ | 2,6-Cl₂-C₆H₃-CH₂- | Oil ¹H—NMR* 5.8 ppm |
| 140 | $CH_3$ | $HC{\equiv}C-CH_2-$ | 2,6-Cl₂-C₆H₃-CH₂- | Oil ¹HNMR* 5.75 ppm |

-continued

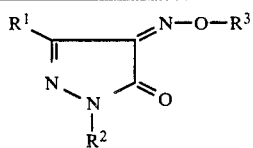

| Example No. | R¹ | R² | R³ | Physical data [M.p. = melting point in °C.] |
|---|---|---|---|---|
| 141 | CH₃ | H₂C=CH—CH₂— | 2,6-dichlorobenzyl | M.p. 80 |
| 142 | CH₃ | NC—CH₂— | 3-methoxybenzyl | Oil ¹H—NMR* 5.5 ppm |
| 143 | CH₃ | NC—CH₂— | 2-cyanobenzyl | Oil ¹H—NMR* 5.65 ppm |
| 144 | CH₃ | NC—CH₂— | 3-cyanobenzyl | Oil ¹H—NMR* 5.5 ppm |
| 145 | CH₃ | NC—CH₂— | 4-cyanobenzyl | M.p. 122 |
| 146 | CH₃ | H₂C=CH—CH₂— | 2-cyanobenzyl | M.p. 83 |
| 147 | CH₃ | H | 2-bromobenzyl | M.p. 126 |
| 148 | CH₃ | HC≡C—CH₂— | 3-bromobenzyl | M.p. 74 |
| 149 | CH₃ | H₂C=CH—CH₂— | 3,4-dichlorobenzyl | Oil ¹H—NMR* 5.4 ppm |
| 150 | CH₃ | HC≡C—CH₂— | 3,4-dichlorobenzyl | Oil ¹H—NMR* 5.4 ppm |
| 151 | CH₃ | H₂C=CH—CH₂ | 2-chlorobenzyl | M.p. 55 |
| 152 | CH₃ | HC≡C—CH₂— | 2-chlorobenzyl | M.p. 77 |

-continued

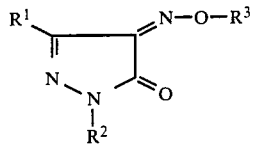
(I)

| Example No. | $R^1$ | $R^2$ | $R^3$ | Physical data [M.p. = melting point in °C.] |
|---|---|---|---|---|
| 153 | $CH_3$ | $NC-CH_2-$ | 2-Br-C$_6$H$_4$-CH$_2$- | M.p. 116 |
| 154 | $CH_3$ | $NC-CH_2$ | 3-Br-C$_6$H$_4$-CH$_2$- | Oil $^1$H—NMR$^+$ 5.5 ppm |
| 155 | $CH_3$ | H | 2-F-C$_6$H$_4$-CH$_2$- | M.p. 72 |
| 156 | $CH_3$ | H | 3-F-C$_6$H$_4$-CH$_2$- | M.p. 94 |
| 157 | $CH_3$ | H | 4-F-C$_6$H$_4$-CH$_2$- | M.p. 115 |
| 158 | $CH_3$ | H | 4-Cl-C$_6$H$_4$-O-CH$_2$- | M.p. 98 |
| 159 | $CH_3$ | $HO-CH_2-CH_2-$ | 4-Cl-C$_6$H$_4$-O-CH$_2$- | M.p. 74 |
| 160 | $CH_3$ | $HO-CH_2-CH_2-$ | 4-Cl-C$_6$H$_4$-CH$_2$- | Oil $^1$H—NMR* 5.4 ppm |
| 161 | $CH_3$ | $HO-CH_2-CH_2-$ | 2,4-Cl$_2$-C$_6$H$_3$-CH$_2$-O- | M.p. 102 |
| 162 | $CH_3$ | $HO-CH_2-CH_2-$ | 3,4-Cl$_2$-C$_6$H$_3$-CH$_2$- | M.p. 99 |
| 163 | $CH_3$ | $HO-CH_2-CH_2-$ | 3-Cl-C$_6$H$_4$-CH$_2$- | Oil $^1$H—NMR$^+$ 5.4 ppm |
| 164 | $CH_3$ | $HO-CH_2-CH_2-$ | 2,3-Cl$_2$-C$_6$H$_3$-CH$_2$- | M.p. 87 |
| 165 | $CH_3$ | $NC-CH_2$ | 2-F-C$_6$H$_4$-CH$_2$- | M.p. 83 |
| 166 | $CH_3$ | $CH_2=CH-CH_2-$ | 2-F-C$_6$H$_4$-CH$_2$- | Oil $^1$H—NMR* 5.5 ppm |

-continued

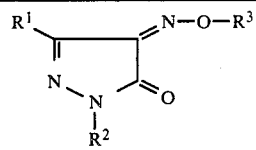

(I)

| Example No. | R¹ | R² | R³ | Physical data [M.p. = melting point in °C.] |
|---|---|---|---|---|
| 167 | $CH_3$ | $NC-CH_2-$ | 3-F-C₆H₄-CH₂- | M.p. 60 |
| 168 | $CH_3$ | $NC-CH_2$ | 4-F-C₆H₄-CH₂- | M.p. 73 |
| 169 | $CH_3$ | $NC-CH_2-$ | 4-Cl-C₆H₄-O-CH₂- | Oil ¹H—NMR* 5.9 ppm |
| 170 | $CH_3$ | $H_2C=CH-CH_2-$ | 4-Cl-C₆H₄-O-CH₂- | Oil ¹H—NMR* 5.9 ppm |
| 171 | $CH_3$ | $HO-CH_2-CH_2-$ | 2-CN-C₆H₄-CH₂- | M.p. 86 |
| 172 | $CH_3$ | $HO-CH_2-CH_2-$ | 3-CN-C₆H₄-CH₂- | M.p. 78 |
| 173 | $CH_3$ | $HO-CH_2-CH_2$ | 4-CN-C₆H₄-CH₂- | M.p. 130 |
| 174 | $CH_3$ | $CH_3$ | 4-Cl-C₆H₄-S-CH₂- | M.p. 72 |
| 175 | $CH_3$ | $NC-CH_2-CH_2-$ | 4-Cl-C₆H₄-S-CH₂- | Oil ¹H—NMR* 5.75 ppm |
| 176 | $CH_3$ | $C_2H_5-O-CO-CH_2-$ | 2,3-Cl₂-C₆H₃-CH₂- | M.p. 83 |
| 177 | $CH_3$ | $HC\equiv C-CH_2-$ | 4-Cl-C₆H₄-CH₂- | M.p. 75 |
| 178 | $CH_3$ | $C_2H_5-O-CO-CH_2-$ | 4-Cl-C₆H₄-CH₂- | Oil ¹H—NMR* 5.4 ppm |
| 179 | $CH_3$ | $HC\equiv C-CH_2-$ | 2,3-Cl₂-C₆H₃-CH₂- | M.p. 97 |
| 180 | $CH_3$ | $C_2H_5-O-CO-CH_2-$ | 2,3-Cl₂-C₆H₃-CH₂- | M.p. 72 |
| 181 | $CH_3$ | $CH_3$ | 4-O₂N-2-Cl-C₆H₃-CH₂- | M.p. 118–120 |

-continued $$\underset{\underset{R^2}{|}}{\overset{R^1}{\underset{N}{\bigvee}}}\overset{N-O-R^3}{\underset{O}{\bigvee}} \quad (I)$$

| Example No. | R¹ | R² | R³ | Physical data [M.p. = melting point in °C.] |
|---|---|---|---|---|
| 182 | CH₃ | CH₃ | NC—⟨C₆H₃(Cl)⟩—CH₂— | M.p. 165-175 |
| 183 | CH₃ | epoxide-CH₂— | ⟨C₆H₄(Cl)⟩—CH₂— | M.p. 68 |
| 184 | CH₃ | epoxide-CH₂— | Cl,Cl-⟨C₆H₃⟩—CH₂— | M.p. 75 |
| 185 | CH₃ | epoxide-CH₂— | Cl-⟨C₆H₄⟩—CH₂— | M.p. 60 |
| 186 | CH₃ | epoxide-CH₂— | Cl,Cl-⟨C₆H₃⟩—CH₂— | M.p. 85 |
| 187 | CH₃ | H₂N—CO—CH₂— | ⟨C₆H₄(Cl)⟩—CH₂— | M.p. 211 |
| 188 | CH₃ | (CH₃)₂N—CO—CH₂— | ⟨C₆H₄(Cl)⟩—CH₂— | Oil ¹H—NMR* 5.6 ppm |
| 189 | CH₃ | CH₃—NH—CO—CH₂— | ⟨C₆H₄(Cl)⟩—CH₂— | M.p. 149 |
| 190 | H | CH₃ | ⟨C₆H₄(Cl)⟩—CH₂— | Oil ¹H—NMR* 5.4 ppm |
| 191 | H | CH₃ | Cl,Cl-⟨C₆H₃⟩—CH₂— | M.p. 92 |
| 192 | H | H | ⟨C₆H₄(Cl)⟩—CH₂— | M.p. 131 |
| 193 | H | H | Cl,Cl-⟨C₆H₃⟩—CH₂— | M.p. 136 |
| 194 | H | CH₃ | Cl-⟨C₆H₄⟩—CH₂— | M.p. 76 |

-continued

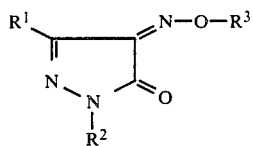
(I)

| Example No. | R¹ | R² | R³ | Physical data [M.p. = melting point in °C.] |
|---|---|---|---|---|
| 195 | H | CH₃ | 2,6-dichlorobenzyl (–CH₂–C₆H₃Cl₂) | M.p. 85 |
| 196 | H | CH₃ | 4-NC–C₆H₄–CH₂– | M.p. 81 |
| 197 | H | CH₃ | 4-Br–C₆H₄–CH₂– | M.p. 84 |
| 198 | H | CH₃ | 4-Cl–C₆H₄–O–CH₂– | M.p. 74 |
| 199 | H | NC–CH₂–CH₂– | 2-Cl–C₆H₄–CH₂– | Oil ¹H—NMR* 6.0 ppm |
| 200 | H | NC–CH₂–CH₂– | 3,4-dichlorobenzyl | Oil ¹H—NMR* 5.3 ppm |
| 201 | H | CH₃ | 4-O₂N–C₆H₄–CH₂– | M.p. 130 |
| 202 | H | CH₃ | 2,4-dimethylbenzyl | Oil ¹H—NMR* 5.5 ppm |
| 203 | H | CH₃ | 4-(F₃C–S)–C₆H₄–CH₂– | Oil ¹H—NMR* 5.5 ppm |
| 204 | H | CH₃ | 2-CF₃–C₆H₄–CH₂– | M.p. 49-51 |
| 205 | H | CH₃ | 4-CF₃-3-Cl–C₆H₃–CH₂– | M.p. 97 |
| 206 | H | CH₃ | 4-Cl-3-CF₃–C₆H₃–CH₂– | Oil ¹H—NMR* 5.45 ppm |
| 207 | H | NC–CH₂–CH₂– | 2,6-dichlorobenzyl | M.p. 116-119 |

-continued
$$\text{(I)}$$
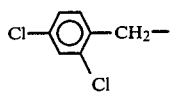
| Example No. | R¹ | R² | R³ | Physical data [M.p. = melting point in °C.] |
|---|---|---|---|---|
| 208 | H | NC—CH₂—CH₂— | 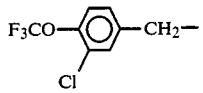 | M.p. 118–120 |
| 209 | H | CH₃ | 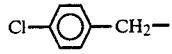 | Oil ¹H—NMR* 5.45 ppm |
| 210 | H | NC—CH₂—CH₂— | 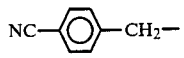 | Oil ¹H—NMR* 5.6 ppm |
| 211 | H | NC—CH₂—CH₂— | 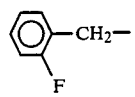 | Oil ¹H—NMR* 5.5 ppm |
| 212 | H | NC—CH₂—CH₂— | 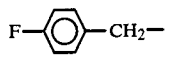 | M.p. 98–100 |
| 213 | H | NC—CH₂—CH₂— | 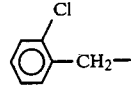 | Oil ¹H—NMR* 5.5 ppm |
| 214 | H | HO—CH₂—CH₂— | 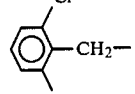 | Oil ¹H—NMR* 5.6 ppm |
| 215 | H | HO—CH₂—CH₂— | 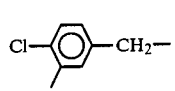 | M.p. 105–108 |
| 216 | H | HO—CH₂—CH₂— |  | Oil ¹H—NMR* 5.4 ppm |
| 217 | H | NC—CH₂—CH₂— | 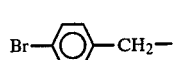 | M.p. 112–114 |
| 218 | H | HO—CH₂—CH₂— | 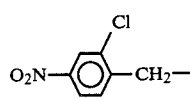 | Oil ¹H—NMR* 5.4 ppm |
| 219 | H | CH₃ | 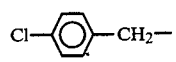 | M.p. 118 |
| 220 | H | HO—CH₂—CH₂— | Cl—⌬—CH₂— | Oil ¹H—NMR* 5.45 ppm |
| 221 | H | HO—CH₂—CH₂— | 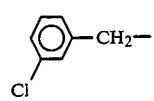 | Oil ¹H—NMR* 5.45 ppm |

-continued
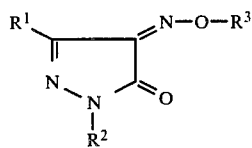
(I)
| Example No. | R¹ | R² | R³ | Physical data [M.p. = melting point in °C.] |
|---|---|---|---|---|
| 222 | H | HO—CH₂—CH₂— | NC-C₆H₄-CH₂— (4-NC-C₆H₄-CH₂—) | M.p. 75 |
| 223 | H | HO—CH₂—CH₂— | 2,3,6-Cl₃-C₆H₂-CH₂— | M.p. 90 |
| 224 | H | HO—CH₂—CH₂— | 2-NC-C₆H₄-CH₂— | Oil ¹H—NMR* 5.6 ppm |
| 225 | H | NC—CH₂—CH₂— | 3-Cl-C₆H₄-CH₂— | Oil ¹H—NMR* 5.4 ppm |
| 226 | H | NC—CH₂—CH₂— | 2,3,6-Cl₃-C₆H₂-CH₂— | M.p. 118–119 |
| 227 | H | NC—CH₂—CH₂— | 4-Cl-C₆H₄-O-CH₂— | M.p. 94 |
| 228 | H | C₆H₅— | 2,6-Cl₂-C₆H₃-CH₂— | M.p. 98–100 |
| 229 | H | C₆H₅— | 2-NC-C₆H₄-CH₂— | M.p. 102–104 |
| 230 | H | C₆H₅— | 4-Cl-C₆H₄-O-CH₂ | M.p. 137–139 |
| 231 | H | H | 3,5-Cl₂-C₆H₃-CH₂— | M.p. 105 |
| 232 | H | H | 2,6-Cl₂-C₆H₃-CH₂— | M.p. 157–159 |
| 233 | H | H | 4-NC-C₆H₄-CH₂— | M.p. 144–146 |

-continued

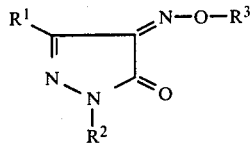

(I)

| Example No. | R¹ | R² | R³ | Physical data [M.p. = melting point in °C.] |
|---|---|---|---|---|
| 234 | H | NC—CH₂— | 2,6-Cl₂-C₆H₃-CH₂— | Oil ¹H—NMR* 5.8 ppm |
| 235 | H | NC—CH₂— | 4-NC-C₆H₄-CH₂— | M.p. 110 |
| 236 | H | CH₃ | 2,3,6-Cl₃-C₆H₂-CH₂— | M.p. 98 |
| 237 | H | C₂H₅—O—CO—CH₂— | 2,6-Cl₂-C₆H₃-CH₂— | M.p. 124 |
| 238 | H | C₂H₅—O—CO—CH₂— | 4-NC-C₆H₄-CH₂— | Oil ¹H—NMR* 5.35 ppm |
| 239 | H | NC—CH₂— | 2,3-Cl₂-C₆H₃-CH₂— | Oil ¹H—NMR* 5.5 ppm |
| 240 | H | C₂H₅—O—CO—CH₂— | 2,3-Cl₂-C₆H₃-CH₂— | M.p. 74 |
| 241 | H | NC—CH₂— | 2-Cl-C₆H₄-CH₂— | Oil ¹H—NMR* 5.66 ppm |
| 242 | H | C₂H₅—O—CO—CH₂— | 2-Cl-C₆H₄-CH₂— | M.p. 64 |
| 243 | H | NC—CH₂— | 3,4-Cl₂-C₆H₃-CH₂— | M.p. 103–105 |
| 244 | H | C₂H₅—O—CO—CH₂— | 3,4-Cl₂-C₆H₃-CH₂— | M.p. 74–75 |
| 245 | H | H | 3-Cl-C₆H₄-CH₂— | M.p. 131 |
| 246 | H | C₆H₅ | 2-Cl-C₆H₄-CH₂— | M.p. 84–6 |

-continued

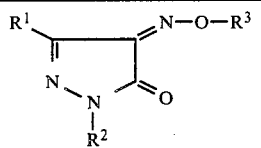
(I)

| Example No. | $R^1$ | $R^2$ | $R^3$ | Physical data [M.p. = melting point in °C.] |
|---|---|---|---|---|
| 247 | H | phenyl | 2,6-dichlorobenzyl (Cl, Cl-C6H3-CH2-) | M.p. 104 |
| 248 | H | -CH2-(epoxide) | 2-chlorobenzyl (Cl-C6H4-CH2-) | $^1$H—NMR* 5.6 ppm |
| 249 | H | CH3 | C4H9 | $^1$H—NMR* 4.3–4.66 ppm |
| 250 | H | CH3 | C3H7 | $^1$H—NMR* 4.2–4.6 ppm |
| 251 | H | CH3 | C5H11 | $^1$H—NMR* 4.3–4.6 ppm |
| 252 | H | CH3 | 2-chloro-4-cyanobenzyl (NC, Cl-C6H3-CH2-) | M.p. 146-9 |
| 253 | H | CH3 | 2-chloro-5-nitrobenzyl (Cl, O2N-C6H3-CH2-) | M.p. 90-2 |
| 254 | CH3 | -CH2-CH2-CN | 2-chloro-5-nitrobenzyl (Cl, NO2-C6H3-CH2-) | M.p. 112 |
| 255 | H | H | 2-chloro-5-nitrobenzyl (Cl, NO2-C6H3-CH2-) | M.p. 143-5 |
| 256 | CH3 | H | 2-chloro-5-nitrobenzyl (Cl, NO2-C6H3-CH2-) | M.p. 179 |
| 257 | CH3 | -CH2-CH2-OH | 2-chloro-5-nitrobenzyl (Cl, NO2-C6H3-CH2-) | M.p. 125-7 |
| 258 | CH3 | H | 3,4-dimethoxybenzyl (H3CO, H3CO-C6H3-CH2-) | M.p. 134-8 |
| 259 | CH3 | CH3 | 3,4-dimethoxybenzyl (H3CO, H3CO-C6H3-CH2-) | $^1$H—NMR* 5.32 ppm |
| 260 | H | -CH2-CH2-CN | 3,4-dimethoxybenzyl (H3CO, H3CO-C6H3-CH2-) | $^1$H—NMR* 5.41 ppm |
| 261 | H | CH3 | 3,4-dimethoxybenzyl (H3CO, H3CO-C6H3-CH2-) | $^1$H—NMR* 5.32 ppm |

-continued

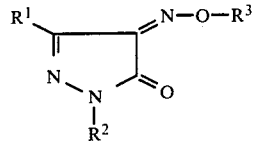
(I)

| Example No. | $R^1$ | $R^2$ | $R^3$ | Physical data [M.p. = melting point in °C.] |
|---|---|---|---|---|
| 262 | CH₃ | —CH₂—CN | Cl, O₂N-phenyl-CH₂— | M.p. 77 |
| 263 | H | —CH₂CN | Cl, O₂N-phenyl-CH₂— | ¹H—NMR* 5.5 ppm |
| 264 | H | —CH₂—CH₂—CN | Cl, O₂N-phenyl-CH₂— | ¹H—NMR* 5.5 ppm |
| 265 | H | CH₃ | 2-Cl, 6-F-phenyl-CH₂— | M.p. 85–105 |
| 266 | H | CH₃ | 3,5-(CH₃)₂-phenyl-CH₂— | ¹H—NMR* 5.4 |
| 267 | H | —C₃H₇ | 2,6-Cl₂-phenyl-CH₂— | M.p. 70 |
| 268 | H | —C₂H₅ | 2,6-Cl₂-phenyl-CH₂— | M.p. 66 |
| 269 | H | —C₄H₉ | 2,6-Cl₂-phenyl-CH₂— | M.p. 74 |
| 270 | CH₃ | —CH₂—COOC₂H₅ | 3-Cl-phenyl-CH₂— | ¹H—NMR* 5.4 |
| 271 | CH₃ | —CH₂—COOC₂H₅ | 2,6-Cl₂-phenyl-CH₂— | ¹H—NMR* 5.75 |
| 272 | H | CH₃ | 3,5-Cl₂-phenyl-CH₂— | ¹H—NMR* 5.5 |

-continued

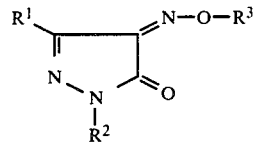

| Example No. | R¹ | R² | R³ | Physical data [M.p. = melting point in °C.] |
|---|---|---|---|---|
| 273 | CH₃ | -CH₂-(epoxide) | 3-Cl-C₆H₄-CH₂- | ¹H—NMR* 5.45 |
| 274 | CH₃ | -CH₂-(epoxide) | 2,3-Cl₂-C₆H₃-CH₂- | ¹H—NMR* 5.8 |
| 275 | CH₃ | -CH₂-CO-NH₂ | 2,3-Cl₂-C₆H₃-CH₂- | M.p. 234 |
| 276 | CH₃ | -CH₂-CO-NH-C₂H₅ | 2,3-Cl₂-C₆H₃-CH₂- | M.p. 141 |
| 277 | CH₃ | -CH₂-CO-N(CH₃)₂ | 2,3-Cl₂-C₆H₃-CH₂- | M.p. 143 |
| 278 | CH₃ | -CH₂-CO-NH₂ | 3-Cl-C₆H₄-CH₂- | M.p. 190 |
| 279 | CH₃ | -CH₂-CO-N(CH₃)₂ | 3-Cl-C₆H₄-CH₂- | ¹H—NMR* 5.4 |
| 280 | CH₃ | -CH₂-CO-NH₂ | 3,4-Cl₂-C₆H₃-CH₂- | M.p. 210 |
| 281 | CH₃ | -CH₂-CO-N(CH₃)₂ | 3,4-Cl₂-C₆H₃-CH₂- | M.p. 132 |
| 282 | CH₃ | -CH₂-CO-NHCH₃ | 4-Cl-C₆H₄-CH₂- | ¹H—NMR* 5.5 |
| 283 | CH₃ | -CH₂-CO-NH₂ | 4-Cl-C₆H₄-CH₂- | M.p. 203 |
| 284 | CH₃ | -CH₂-CO-N(CH₃)₂ | 4-Cl-C₆H₄-CH₂- | M.p. 134 |
| 285 | CH₃ | -CH₂-CO-NH-C₂H₅ | 4-Cl-C₆H₄-CH₂- | M.p. 150 |

-continued

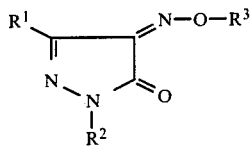
(I)

| Example No. | R¹ | R² | R³ | Physical data [M.p. = melting point in °C.] |
|---|---|---|---|---|
| 286 | $CH_3$ | $-CH_2-CO-OCH_3$ | 2,6-dichlorobenzyl | M.p. 95 |
| 287 | $CH_3$ | $-CH_2-CO-OCH_3$ | 3,4-dichlorobenzyl | M.p. 131 |
| 288 | H | $CH_3$ | 2-chloro-6-cyanobenzyl | M.p. 122 |
| 289 | $CH_3$ | $CH_3$ | 2-chloro-6-cyanobenzyl | M.p. 148 |
| 290 | $CH_3$ | $-CH_2-COOCH_3$ | 3-chlorobenzyl | $^1$H—NMR* 5.5 |
| 291 | $CH_3$ | $-CH_2-CH_2-CN$ | 2-chloro-6-cyanobenzyl | M.p. 130 |
| 292 | $CH_3$ | $-CH_2-CH_2-OH$ | 2-chloro-6-cyanobenzyl | M.p. 149 |
| 293 | H | H | 2-chloro-6-cyanobenzyl | M.p. 176 |
| 294 | $CH_3$ | H | 2-chloro-6-cyanobenzyl | M.p. 140 |
| 295 | $CH_3$ | $-CH_2-COOCH_3$ | 4-chlorobenzyl | M.p. 117 |
| 296 | $CH_3$ | $-CH_2-CN$ | 2-chloro-6-cyanobenzyl | M.p. 117 |
| 297 | $CH_3$ | H | 2,6-dichlorobenzyl | M.p. 140 |

-continued

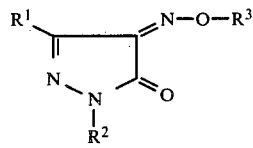

| Example No. | R¹ | R² | R³ | Physical data [M.p. = melting point in °C.] |
|---|---|---|---|---|
| 298 | CH₃ | H | 2,5-dichlorobenzyl (Cl, Cl on ring; CH₂—) | M.p. 135 |
| 299 | H | CH₃ | 2,3-dichlorobenzyl | M.p. 121 |
| 300 | H | CH₃ | 2,5-dichlorobenzyl | M.p. 98 |
| 301 | CH₃ | CH₃ | 2,3-dichlorobenzyl | M.p. 125 |
| 302 | CH₃ | CH₃ | 2,5-dichlorobenzyl | M.p. 122 |
| 303 | CH₃ | —CH₂—CN | 2,3-dichlorobenzyl | M.p. 129 |
| 304 | CH₃ | —CH₂—(oxiranyl) | 2,3-dichlorobenzyl | M.p. ~85 |
| 305 | CH₃ | —CH₂—CN | 2,5-dichlorobenzyl | M.p. 116 |
| 306 | CH₃ | —CH₂—(oxiranyl) | 2,5-dichlorobenzyl | M.p. ~60 |
| 307 | CH₃ | —CH₂CH₂CN | 2,3-dichlorobenzyl | M.p. 104 |
| 308 | CH₃ | —CH₂CH₂CN | 2,5-dichlorobenzyl | ¹H—NMR* 5.5 |

-continued

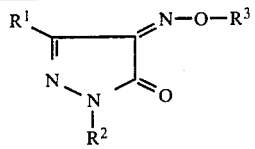
(I)

| Example No. | R¹ | R² | R³ | Physical data [M.p. = melting point in °C.] |
|---|---|---|---|---|
| 309 | H | H | 2,3-dichlorobenzyl (Cl, Cl on ring, CH₂—) | M.p. 179 |
| 310 | H | H | 2,5-dichlorobenzyl | M.p. 158 |
| 311 | CH₃ | —CH₂—OH | 3,4-dichlorobenzyl | $^1$H—NMR* 5.4 |
| 312 | CH₃ | —CH₂—CH=CH₂ | 2,5-dichlorobenzyl | M.p. 91 |
| 313 | H | H | 2-chloro-6-fluorobenzyl | M.p. 151–4 |
| 314 | H | —C₂H₅ | 2-chloro-5-nitrobenzyl | M.p. 92 |
| 315 | H | —C₄H₉ | 2-chloro-5-nitrobenzyl | $^1$H—NMR* 5.5 |
| 316 | H | —CH₂—CH₂—CH₂—CH₃ | 2,6-dimethylbenzyl | $^1$H—NMR* 5.5 |
| 317 | H | —C₂H₅ | 4-fluorobenzyl | $^1$H—NMR* 5.4 |
| 318 | H | —C₄H₉ | 2,4-dichlorobenzyl | $^1$H—NMR* 5.4 |
| 319 | H | —CH₂—CH=CH₂ | 2,4-dichlorobenzyl | M.p. ~64 |
| 320 | H | —CH₂-epoxide | 2-chloro-6-fluorobenzyl | $^1$H—NMR* 5.7 |

-continued

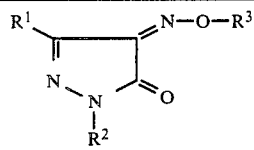

| Example No. | R¹ | R² | R³ | Physical data [M.p. = melting point in °C.] |
|---|---|---|---|---|
| 321 | H | —C₂H₅ | 2-F, 6-Cl-benzyl (F ortho, Cl ortho, CH₂—) | ¹H—NMR* 5.7 |
| 322 | H | —C₃H₇ | 2-F, 6-Cl-benzyl | ¹H—NMR* 5.7 |
| 323 | H | —C₄H₉ | 2-F, 6-Cl-benzyl | ¹H—NMR* 5.7 |
| 324 | H | —CH₂—CH=CH₂ | 2-F, 6-Cl-benzyl | ¹H—NMR* 5.7 |
| 325 | H | —CH₂—CH₂—OH | 3-Cl, 4-NO₂-benzyl | ¹H—NMR* 5.5 |

*The ¹H—NMR spectra were recorded in CDCl₃ with tetramethylsilane as the internal standard. As a rule, the chemical shifts are given, as δ values, for the grouping $\rangle =N-O-CH_2-$.

USE EXAMPLES

The compounds shown below were employed as the comparison substances in the use examples which follow:

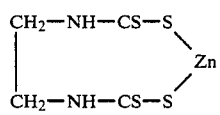

(A)

zinc ethylene-1,2-bis-(dithiocarbamate) and

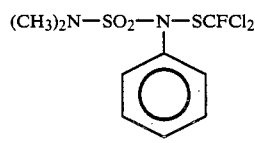

(B)

N,N-dimethyl-N'-(fluordichloromethylthio)-N'-phenyl sulfamide.

Example A

Phytophthora test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabinet at 100% relative atmospheric humidity and at about 20° C.

Evaluation is carried out 3 days after the inoculation.

In this test, a clearly superior activity compared with the prior art is shown, for example, by the compound according to preparation example: 9.

Example B

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to preparation examples: 1, 12, 14, 163, 192, 193, 200, 201, 206, 212, 213, 214 and 215.

Example C

Pyricularia test (rice)/systemic

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants, have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to preparation examples: 2, 11 and 16.

Example D

Cochliobolus sativus test (barley)/protective

Solvent: 100 parts by weight of dimethylformamide
Emulsifier: 0.25 parts by weight alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain in an incubation cabinet for 48 hours at 20° C. and 100% relative atmospheric humidity.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to preparation examples: 1, 2, 9, 15, 16, 17, 18, 19 and 21.

Example E

Botrytis test (beans)/protective

Solvent: 4.7 parts by weight acetone
Emulsifier: 0.3 parts by weight alkylarylpolyglycolether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humidity chamber at 20° C. 3 days after the inoculation, the size of the infected spots on the leaves is evaluated.

In this test, a clearly superior activity compared with the prior art is shown, for example, by the compounds according to the preparation examples: 191, 192, 193, 194, 197, 201, 203, 204, 205 and 206.

Example F

*Leptosphaeria nodorum*-test (wheat)/protective

Solvent: 100 parts by weight of dimethylformamide
Emulsifier: 0.25 parts by weight of alkylarylpolyglycolether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidium suspension of *Leptosphaeria nodorum*. The plants remain in an incubation cabinet at 20° C. and 100% relative atmospheric humidity for 48 hours.

The plants are placed in a greenhouse at a temperature of about 15° C. and a relative atmospheric humidity of about 80%.

Evaluation is carried out 10 days after the inoculation.

In this test, a clearly superior activity compared with the prior art is shown, for example, by the compounds according to the preparation examples: 190, 191, 192 and 193.

It will be understood that the specification and examples are illustrative but not limitative of the present invention and that other embodiments within the spirit and scope of the invention will suggest themselves to those skilled in the art.

What is claimed:

1. A substituted-pyrazolin-5-one of the formula $$\begin{array}{c} R^1 \diagdown \diagup N-O-R^3 \\ \| \\ N \diagdown N \diagup =O \\ | \\ R^2 \end{array}$$

in which
$R^1$ is hydrogen or alkyl with 1 to 8 carbon atoms, $R^2$ is hydrogen, alkyl, alkenyl, alkinyl, cyanoalkyl, hydroxyalkyl, alkoxyalkyl, hydroxycarbonylalkyl, alkoxycarbonylalkyl, aminocarbonylalkyl, alkylaminocarbonylalkyl or dialkylaminocarbonylalkyl with in each case up to 8 carbon atoms in the individual alkyl, alkenyl or alkinyl moieties, or is oxiranylalkyl with 1 to 4 carbon atoms in the alkyl moiety or is optionally substituted carbocyclic aryl or carbocyclic aralkyl each of which has 6 to 10 carbon atoms in the aryl part and 1 to 4 carbon atoms in the alkyl part when present, the optional aryl substituents being halogen, cyano, nitro, hydroxyl, alkyl, alkoxy, dioxyalkylene, alkylcarbonyloxy or alkylthio with in each case up to 4 carbon atoms, halogenoalkyl, halogenoalkoxy or halogenoalkylthio with in each case up to 4 carbon atoms and up to 9 identical or different halogen atoms, and/or phenyl, and $R^3$ is alkyl with 1 to 20 carbon atoms, alkenyl, alkinyl, cyanoalkyl, hydroxyalkyl, alkoxyalkyl, hydroxycarbonylalkyl or alkoxycarbonylalkyl with in each case up to 8 carbon atoms in the individual alkyl, alkenyl or alkinyl moieties, or is cycloalkyl with 3 to 7 carbon atoms or cycloalkylalkyl with 3 to 6 carbon atoms in the cycloalkyl moiety and 1 or 2 carbon atoms in the alkyl moiety, or is carbocyclic arylalkyl, carbocyclic aryloxyalkyl or carbocyclic arylthioalkyl with in each case 1 to 4 carbon atoms in the individual alkyl moities and 6 to 10 carbon atoms in the aryl moities, and in each case optionally substituted by those substituents mentioned for $R^2$, but wherein $R^3$ is methyl or ethyl only if $R^1$ and/or $R^2$ is not hydrogen or methyl with the proviso that when $R^1$ is methyl and $R^2$ is H or phenyl, $R^3$ cannot be benzyl.

2. A substituted pyrazolin-5-one according to claim 1, in which $R^1$ is hydrogen, methyl, ethyl, n- or i-propyl or n-, i-, s- or t-butyl, $R^2$ is hydrogen, methyl, ethyl, n- or i-propyl, n-, i-, s- or t-butyl, ally, butenyl, propargyl, cyanomethyl, cyanoethyl, hydroxymethyl, hydroxyethyl, methoxymethyl, methoxyethyl, ethoxymethyl, ethoxyethyl, hydroxycarbonylmethyl hydroxycarbonylethyl, methoxycarbonylmethyl, methoxycarbonylethyl, ethoxycarbonylmethyl or ethoxycarbonylethyl, or is phenyl or benzyl in each case optionally mono-, di- or tri-substituted by fluorine, chlorine, bromine, iodine, cyano, nitro, hydroxyl, methyl, ethyl, n- or i-propyl, n-, i-, s- or t-butyl, methoxy, ethoxy, dioxymethylene, dioxyethylene, methylthio, ethylthio, acetoxy or propionyloxy, chloromethyl, dichloromethyl, trichloromethyl, trifluoromethyl, dichlorofluoromethyl, chlorodifluoromethyl, trifluoromethoxy, trifluoromethylthio and/or phenyl, and $R^3$ is methyl, ethyl, n- or i-propyl, n- or i-butyl, n- or i-pentyl, n- or i-hexyl, n- or i-heptyl, n- or i-octyl, n- or i-nonyl, n- or i-decyl n- or i-dodecyl, n- or i-hexadecyl, allyl, butenyl, propargyl, cyanomethyl, cyanoethyl, hydroxymethyl, hydroxyethyl, methoxymethyl, methoxyethyl, ethoxymethyl, ethoxyethyl, hydroxycarbonylmethyl, hydroxycarbonylethyl, methoxycarbonylmethyl, methoxycarbonylethyl, ethoxycarbonylmethyl, ethoxycarbonylethyl, cyclopropyl, cyclopentyl, cyclohexyl or cyclohexylmethyl, or is a radical of the formula $$Ar—(Z)_m—(CH_2)_n—,$$

Ar is phenyl or naphthyl optionally substituted up to three times by those substituents named for $R^2$, Z is oxygen or sulphur, m is 0 or 1 and n is 1, 2 or 3, but wherein $R_3$ is methyl or ethyl onyl if $R^1$ and/or $R^2$ is not hydrogen or methyl.

3. A compound according to claim 1, wherein such compound is 4-(2-chlorobenzyloximino)-1,3-dimethylpyrazolin-5-one of the formula

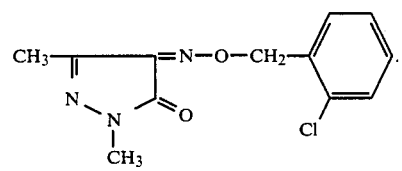

4. A compound according to claim 1, wherein such compound is 4-(2-chloromethyl-benzyloximino)-1,3-dimethylpyrazolin-5-one of the formula

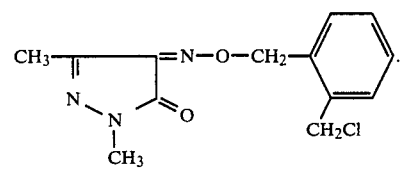

5. A compound according to claim 1, wherein such compound is 4-(4-chlorobenzyloximino)-3-methyl-1-phenylpyrazolin-5-one of the formula

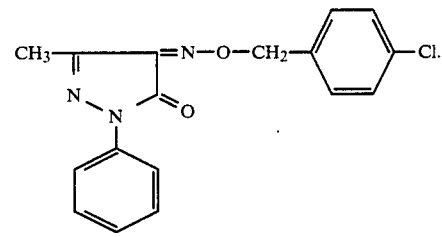

6. A compound according to claim 1, wherein such compound is 4-(2-chlorobenzyloximino)-pyrazolin-5-one of the formula

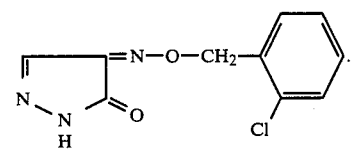

7. A compound according to claim 1, wherein such compound is 4-(3,4-dichlorobenzyloximino)-pyrazolin-5-one of the formula 8. A compound according to claim 1, wherein such compound is 1-cyanoethyl-4-(4-fluorobenzyloximino)-pyrazolin-5-one of the formula

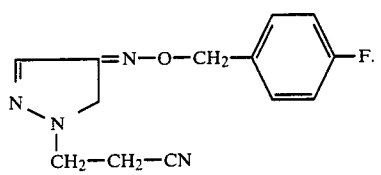

9. A compound according to claim 1, wherein such compound is 4-(2-chlorobenzyloximino)-1-hydroxyethylpyrazolin-5-one of the formula

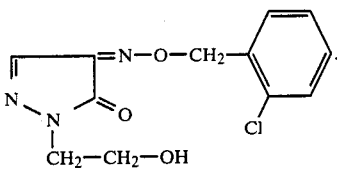

10. A fungicidal composition comprising a fungicidally effective amount of a compound according to claim 1 in admixture with a diluent.

11. A method of combating fungi which comprises administering to such fungi or to a fungus habitat a fungicidally effective amount of a compound according to claim 1.

12. The method according to claim 11, wherein such compound is
4-(2-chlorobenzyloximino)-1,3-dimethyl-pyrazolin-5-one,
4-(2-chloromethyl-benzyloximino)-1,3-dimethyl-pyrazolin-5-one,
4-(4-chlorobenzyloximino)-3-methyl-1-phenyl-pyrazolin-5-one,
4-(2-chlorobenzyloximino)-pyrazolin-5-one,
4-(3,4-dichlorobenzyloximino)-pyrazolin-5-one,
1-cyanoethyl-4-(4-fluorobenzyloximino)-pyrazolin-5-one, or
4-(2-chlorobenzyloximino)-1-hydroxyethyl-pyrazolin-5-one.

* * * * *

UNITED STATES PATENT AND TRADEMARK OFFICE
CERTIFICATE OF CORRECTION

PATENT NO. : 4,666,933

DATED : May 19, 1987

INVENTOR(S) : Klaus Jelich, et al.

It is certified that error appears in the above-identified patent and that said Letters Patent is hereby corrected as shown below:

| | |
|---|---|
| Title Page, under "Related U.S. Application Data" and Col. 1, line 6 | Delete "May 9, 1985" and substitute --May 16, 1985-- |
| Col. 3, line 29 | Delete "artoms" and substitute --atoms-- |
| Col. 5, line 54 | Delete "hydroxyimino" and substitute --hydroximino-- |
| Col. 6, line 23 | Bottom right of first structure delete 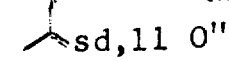 and substitute " 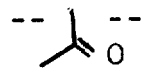 " |
| Col. 7, line 2 | Delete "to" and substitute --at-- |
| Col. 8, line 66 | Before "the presence" insert --in-- |
| Col. 9, line 32 | Correct spelling of --example-- |
| Col. 9, line 58 | Before "rust" insert --against-- |
| Col. 59, line 54 | Delete "zinc" and substitute --Zinc-- |
| Col. 64, line 10 | Correct spelling of --only-- |

UNITED STATES PATENT AND TRADEMARK OFFICE
CERTIFICATE OF CORRECTION

PATENT NO. : 4,666,933

DATED : May 19, 1987

INVENTOR(S) : Klaus Jelich, et al.

It is certified that error appears in the above-identified patent and that said Letters Patent is hereby corrected as shown below:

Col. 65, line 22    Bottom right of first structure insert -- 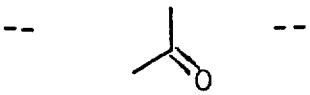 -- as follows:

Signed and Sealed this

Fifteenth Day of December, 1987

Attest:

DONALD J. QUIGG

Attesting Officer    Commissioner of Patents and Trademarks